United States Patent [19]

Anderson et al.

[11] 4,044,027

[45] Aug. 23, 1977

[54] MALEIC ANHYDRIDE PROCESS

[75] Inventors: Robert G. Anderson, San Rafael; Alan E. Straus, El Cerrito; John B. Wilkes, Richmond, all of Calif.

[73] Assignee: Chevron Research Company, San Francisco, Calif.

[21] Appl. No.: 718,235

[22] Filed: Aug. 27, 1976

[51] Int. Cl.$^2$ .......................................... C07D 307/60
[52] U.S. Cl. ............................................... 260/346.75
[58] Field of Search ................ 260/346.8 A, 346.8 M

[56] References Cited

U.S. PATENT DOCUMENTS 3,904,652  9/1975  Frank ........................... 260/346.8 A Primary Examiner—Henry R. Jiles
Assistant Examiner—Bernard Dentz
Attorney, Agent, or Firm—D. A. Newell; John Stoner, Jr.; W. Keith Turner

[57] ABSTRACT

In a process for the conversion of normal butane to maleic anhydride at a pressure between about 15 and 100 psig and a temperature above 675° F, by contacting the normal butane with an oxygen-containing gas and an oxidation catalyst disposed in a fixed catalyst bed or set of tubes in a reactor vessel, and withdrawing an effluent comprising unreacted normal butane, oxygen, Co, $Co_2$, $N_2$ and maleic anhydride from the catalyst bed or tubes, improvements in yield, product quality and plant operability are obtained by rapidly cooling the effluent gas to a temperature below 675° F. One method of accomplishing this is by contacting the effluent gas with cooling coils contained within the reactor but below the catalyst bed.

11 Claims, 2 Drawing Figures

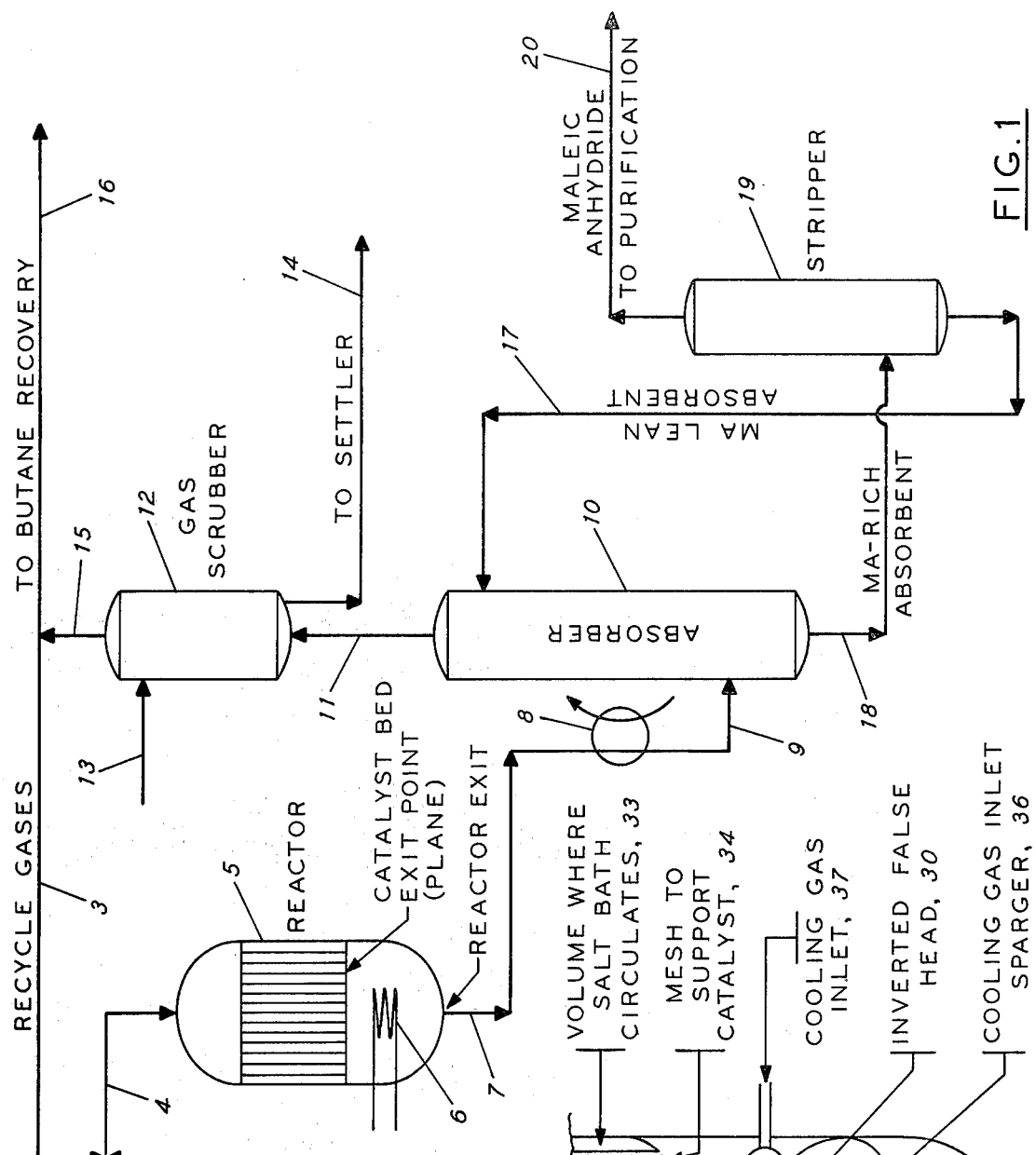

MALEIC ANHYDRIDE PROCESS

BACKGROUND OF THE INVENTION

The present invention relates to the production of maleic anhydride from normal butane.

Prior processes for the conversion of butane to maleic anhydride include, for example, Bergman et al., U.S. Pat. No. 3,293,268 "Production of Maleic Anhydride by Oxidation of n-Butane." According to Bergman et al., the oxidation of normal butane is carried out by contacting the normal butane with oxygen gas and a phosphorus vanadium oxide catalyst at a temperature between 500° and 600° C (932° to 1,112° F). To assure maintaining the temperature within about 932° to 1,112° F in the catalyst-filled reactor tubes, Bergman et al. suggest using a molten salt bath mixture. Such a molten salt bath circulates outside the tubes, that is, on the shell side of a shell and tube heat exchanger type configuration with the catalyst located inside the tubes. See further in this regard Frank, U.S. Pat. No. 3,904,652.

Schneider, U.S. Pat. No. 3,864,280 also discloses oxidation of normal butane to maleic anhydride using a catalyst comprising vanadium and phosphorus oxides.

Prior to Bergman et al. and Schneider, little disclosure had been made of catalytic processes for oxidation of normal butane to maleic anhydride. Thus, as pointed out in the Bergman et al. patent, various oxidation catalysts had been used for oxidation of benzene or butene to maleic anhydride, but generally not for oxidation of normal butane because relatively poor yields of maleic anhydride were obtained when normal butane was used as the feedstock. See also in this regard, U.S. Pat. No. 2,691,606 indicating that benzene and butene were commercially exploited as feedstocks rather than paraffins such as normal butane because it had been found more difficult to oxidize normal butane to maleic anhydride.

The pressure typically used in prior art processes was that sufficient to drive the product gas stream through a water scrubber, about 1 to 5 psig.

Brown et al., *Proc. Roy. Soc.*, Ser. A, 326, 215–227 (1972) disclosed oxidation of benzene to maleic anhydride with further reaction taking place in the catalyst bed and in free space after the catalyst bed at a temperature of 779° F.

SUMMARY OF THE INVENTION

According to the present invention, in a process for the conversion of normal butane to maleic anhydride at a pressure between about 15 and 100 psig and a temperature above 675° F, by contacting the normal butane with oxygen-containing gas in the presence of an oxidation catalyst disposed in a fixed catalyst bed or in a set of tubes in a reactor vessel, and withdrawing an effluent comprising unreacted normal butane, CO, Co$_2$, N$_2$, H$_2$O, oxygen and maleic anhydride from the catalyst bed or tubes, the improvement is made which comprises cooling the effluent gas below 675° F before the effluent is withdrawn from the reactor vessel. Typically, catalyst bed temperature and the effluent from the catalyst bed or tubes is about 675° to 1000° F, usually 700° to 850° F. Thus, in this embodiment of the present invention this effluent must be cooled about 25° F to 175° F or more before the effluent is withdrawn from the reactor vessel.

The apparatus for oxidizing butane to maleic anhydride comprises a large vessel in which there are a multitude of catalyst-filled tubes surrounded by a heat transfer medium. As used in the present application, the term "reactor vessel" includes not only the catalyst-filled tubes, but also the shell which surrounds and holds the tubes in place. Thus, the upper manifold space for distributing the incoming gas steam, the catalyst tubes, and the space below the catalyst tubes in which the effluent gas from each catalyst tube is combined prior to exiting, are all part of the reactor vessel.

In a preferred method of oxidation of n-butane, the conversion of butane per pass is limited, generally, to less than 50% and usually to about 15 to 30%, see for example, commonly assigned co-pending patent application Ser. No. 645,585. Operation at low conversions in turn requires a high percentage of butane in the feed gas to obtain the same productivity (quantity of product per quantity of catalyst) from a given catalyst charge as is obtained in a high conversion process. Butane concentration can be safely increased above 1.5% by volume by simultaneously reducing the oxygen content of the feed gas to considerably less than 20%. Thus, at 10% oxygen, the feed gas may contain any quantity of butane without becoming inflammable at atmospheric pressure. Finally, with a feed gas of low oxygen content, the pressure on the system must be raised in order to restore the oxygen partial pressure to its usual level of about 2.9 psia. Accordingly, it is preferred to operate at a somewhat elevated pressure in the oxidation reactor, usually above 15 psig, and more typically at an exit pressure in the range 20 to 50 psig, so that the oxygen partial pressure is in the desired range and so that there is sufficient driving force to move the reactor effluent in gas phase through the absorber recovery system.

Among other factors, the present invention is based on our findings that, in converting normal butane to maleic anhydride in an oxidation reactor operated between 15 and 100 psig, cooling the reactor effluent to below 675° F, preferably below 625° F, promptly upon the exit of the effluent from the reactor tubes, results in substantially less loss of normal butane to by-products. In addition, without the cooling of the reactor effluent to below 675° F in accordance with the present invention, we have found that there is severe lowering of product quality by formation of color bodies, compounds such as formaldehyde and formic acid, and formation of solids which can plug an aqueous recovery system, and badly contaminate and plug a recycle organic solvent recovery system used to recover maleic anhydride from the reactor effluent.

We have found that at pressures greater than 10 psig, for example, in the range 15 to 50 psig, there is significant conversion of normal butane to undesired by-products, such as carbon dioxide, formaldehyde, etc., unless the effluent is cooled in less than about 1 second after leaving the catalyst bed, preferably less than about ½ second "residence time." The residence time between the catalyst bed exit and the point where the gas has been cooled to a temperature of about 675° to 580° F is calculated for purposes of the present invention by the simplified method of dividing the gas flow rate into the volume of the space through which the gas flows prior to the point where it is at the desired cooled temperature; thus this volume is the postcatalyst bed space inside the reactor, and the exit piping up to the point where the cooling below 675° F (preferably below 580° F) is completed.

Rather than the use of the sharply truncated one-second or ½-second residence time, according to an alternate preferred embodiment, we have found that the equation for $t_1$, given below, more continuously determines the maximum length of time for which the reactor effluent can be held at a given temperature before uncatalyzed oxidation is initiated.

$$t_1 = 1.4 \times 10^{-6} \exp(14350/T) \tag{1}$$

wherein $t_1$ is in seconds and $T$ is the effluent gas temperature at the exit of the reactor tubes in degrees Rankin.

In equation (1) the terminology "exp(14350/T)" means $e$ to the power (14350/T). For a temperature of 675° F (1135° R) the equation (1) formula calculates a time $t_1$ of 0.43 second. Equation (1) gives a conservative answer and hence for the broader general definition of the present invention we have used the 1 second and preferably ½ second maximum post reactor residence time above 675° F–580° F.

Equation (1) is particularly applicable for pressures in the range of 15 to 35 psig; butane concentrations in the range of 1.0 to 3.0 volume %, and oxygen concentrations in the reactor effluent in the range of 5 to 10 volume %.

In a preferred embodiment of the present invention, the effluent gas is cooled by contact with cooling coils contained within the reactor, but below the catalyst bed. Generally, the cooling medium will be water which is passed through the cooling coils at a rate sufficient to lower the temperature of the exit gas to a value below 675° F, preferably below 625° F and most preferably below 580° F.

In an alternate preferred embodiment, instead of using cooling coils in the bottom of the reactor, the catalyst effluent gases can be cooled promptly by injecting a portion of cooled reactor effluent gases into the bottom of the reactor, i.e. by mixing a quench gas with the catalyst bed effluent gas to do the required cooling.

A third alternative is to markedly reduce the amount of empty space in the reactor after the catalyst bed exit point so that a cooler outside of the reactor will be reacted sufficiently soon to cool the catalyst bed effluent gases below the critical temperature of 675°–580° F within about 1 to ½ second more preferably within a residence time maximum as given by equation (1).

The various modes mentioned above for cooling the catalyst bed effluent gas within the time $t$, as given by equation (1) can be combined so that a combination of one, two or three of the modes is used.

Thus, according to the present invention, the volume between the catalyst bed outlet and the point at which the effluent gas is cooled to below 675° F, preferably below 625° F and most preferably below 580° F, and/or other conditions, such as the amount and/or temperature of the cooling gas, area and heat transfer coefficient of cooling coils, etc., are adjusted or maintained so that the time above the critical temperature of 675° to 580° F is less than a time $T_1$ given by the above equation (eq. 1).

The actual time above a certain temperature is difficult to calculate precisely because of geometric factors and because of difficulty in precisely calculating the gas cooling time. However, with certain assumptions, a time, $t_o$, for cooling the effluent by mixing with a quench gas, can be defined as follows:

$$t_o = \frac{V}{V_{mix}} \tag{2}$$

Also, temperature of the mixed gases can be defined as follows:

$$T_{mix} = \frac{v_1 \times T_1 + v_2 \times T_2}{v_{mix}} \tag{3}$$

In equations (2) and (3), $t_o$ is time in seconds, $V$ is the volume of empty space in reactor below the catalyst tubes, $T_1$ and $v_1$ are temperature and volume of gas per unit time at the exit from catalyst tubes, $T_2$ and $v_2$ are temperature and volume of cooling gas per unit time, $V_{mix}$ is equal to $v_1 + V_2$, and $T_{mix}$ is the temperature of the mixed effluent and cooling gases.

It is to be noted that the time, $t_o$, above 675° to 580° F assumes that the time is unaltered by the method of introducing the cooling gas. This assumption is conservative for purposes of successfully carrying out the process of the present invention because various modes of introducing the cooling gas should generally reduce the time, $t_o$, to reach the equilibrium temperature, i.e. cool below the critical range of 580°–675° F, compared to the time calculated for only one injection point for the cooling gas.

In the embodiment where cooling gas is not used to cool the reactor effluent equation (4) below, which is similar to equation (2), is used to define the residence time between the catalyst bed exit point and the point at which the cooling has been accomplished.

$$t_o = V/V \tag{4}$$

where $V$ is the volume of empty space between the catalyst bed exit point and the point at which the cooling to below 675° F, preferably below 625° to 580° F, has been accomplished, and $v$ is the actual flow rate per unit time of the effluent from the catalyst bed.

BRIEF DESCRIPTION OF THE DRAWINGS

FIG. 1 is a schematic process flow diagram illustrating a preferred embodiment of the present invention.

FIG. 2 is a schematic diagram illustrating the lower part of a shell and tube type reactor adopted so as to utilize cooling gases in the present invention.

FURTHER DESCRIPTION OF THE DRAWINGS

Referring in more detail to FIG. 1, fresh feed normal butane is introduced to the process via line 1 and then into reactor 5 via line 4. Before introduction to reactor 5 the feed normal butane is combined with recycle gases as indicated by line 3 and air as indicated by line 2.

In place of using air, a gaseous stream containing oxygen may be used in the process. Thus an enriched oxygen stream may be used in place of the air or in place of a part of the air, which in both instances will effect a reduction in the amount of diluent nitrogen passing through reactor 5.

The oxidizer reactor 5 consists of conventional heat exchanger type design with catalyst packed in tubes surrounded by a heat transfer liquid, usually a molten salt mixture. The process flow diagram is schematic only.

The normal butane fed to reactor 5 is oxidized in the presence of a catalyst effective for accelerating the reaction of normal butane with oxygen to form maleic anhydride. Preferred catalysts comprise mixed oxides of vanadium and phosphorus, especially those described in the previously cited U.S. Pat. No. 3,864,280, and preferred reaction temperatures are in the range 700°–800° F.

The reactor pressure preferably is between about 15 and 50 psig, more preferably between about 15 and 35 psig, at the outlet or bottom head of the reactor.

Following the oxidation reaction in the reactor there must be sufficient pressure so that the gaseous effluent can flow through line 7 and, after maleic absorption in absorber 10, can continue onward to the recycle gas compressor.

The process of the present invention has particular application to a system wherein the maleic anhydride is recovered from the reactor effluent using an organic absorbent as opposed to an aqueous recovery system. Reactors using aqueous recovery systems can be operated at lower pressure, typically below about 10 psig, compared to the pressure desired at the reactor outlet when organic solvent recovery systems are used.

We have found that decomposition of normal butane after exiting from the catalyst bed is particularly acute and detrimental in a normal butane conversion process operated at the somewhat higher pressures necessitated by the use of an organic solvent recovery system. Still further in this regard, it is especially preferred to employ the process of the present invention in the context of a recycle process wherein at least a portion of the absorber effluent gas is recycled to the oxidizer reactor inlet. Economical use of such recycle operation also generally necessitates the use of somewhat higher pressures (compared to nonrecycle processes) in the oxidizer reactor so that the reactor off gas will reach a recycle compressor at a sufficiently high pressure. For example, we have found a pressure above about 20 psig is desirable in the reactor when using recycle operation and an organic absorber for maleic anhydride recovery. A typical pressure drop profile starting at the reactor bottom in line 7 is as follows:

|        | Pressure (psig) |
|--------|-----------------|
| Line 7  | 24 |
| Line 9  | 22 |
| Line 11 | 21 |
| Line 15 | 20 |
| Line 3  | 42 |

Referring again to the reactor, the effluent is withdrawn from the catalyst bed at the bottom of the bed (as indicated, at the "catalyst bed exit point" or plane of exit from the catalyst tubes) and the effluent preferably is cooled by cooler 6 so that the effluent leaves the reactor (as indicated at the "reactor exit") at a temperature below 675° F, most preferably below 580° F. The gaseous effluent withdrawn from the reactor in line 7 is further cooled in gas cooler 8, usually to about 275° F, and then at least a portion of the effluent is fed to absorber 10, which contains organic solvent.

According to one alternate preferred embodiment of the present invention, instead of or in addition to use of cooler 6 a portion of the cooled effluent in line 9 is recycled to the bottom portion of the reactor. Preferably in this mode of operation this portion of the reactor effluent is further cooled in a heat exchanger to increase its effectiveness in lowering the gas mixture outlet temperature from the reactor.

Alternate modes of cooling the effluent from the catalyst tubes in reactor 5 may be used in addition to, or in place of, the mode wherein the reactor effluent is cooled by cooler 6. The catalyst bed effluent can be cooled by introducing a portion of the feed air or oxygen-containing feed stream 2 to the outlet head of the reactor; a third alternate preferred embodiment is that wherein a portion of the recycle gas of line 3 is used as the cooling gas. Any of these three streams can be used to effect the cooling, and still further means such as injection of liquid normal butane to the outlet head of the reactor or combinations of one or more of these methods or like methods can be used to effect the required cooling at the outlet of the catalyst beds in reactor 5.

According to a particularly preferred alternate embodiment of the present invention the recycle gas as indicated by line 3 is used to effect the cooling.

The terminology "recycle gas" is used herein to mean effluent gas from the reactor after maleic anhydride has been removed from it. As shown in the preferred embodiment illustrated in the drawing, the recycle gas also has been treated by a water scrubbing operation in gas scrubber 12, but this is not necessarily included in a generalized version of the process.

Referring again to the effluent gas from the reactor, after cooling in exchanger 8 it is introduced to absorber 10. In absorber 10 it is countercurrently contacted with an organic solvent in a multistage absorber column. The organic solvent is introduced via line 17 to the absorber and selectively absorbs maleic anhydride from the countercurrently flowing gas which enters the absorber via line 9 and exits via line 11. The maleic anhydride-rich solvent leaves the absorber via line 18 and is passed to stripper 19.

In stripper 19 maleic anhydride is stripped out of the organic absorbent in conventional fashion and then, after further purification, maleic anhydride is withdrawn as the product. The stripped maleic anhydride-lean organic solvent is removed from the bottom of the stripper and recycled to the absorber via line 17.

The reactor effluent gases which have been substantially freed of maleic anhydride are passed via line 11 from the top of the absorber to gas scrubber 12 where they are treated by water introduced through line 13 for removal of trace contaminants.

Referring now to FIG. 2, a schematic sketch is shown of the bottom of reactor 5 in modified form to achieve reduced residence time in the reactor and with a sparger means for introducing a quench gas to the bottom of the reactor. According to this alternate preferred embodiment of the present invention, the residence time in the bottom of reactor 5 is reduced by inverted false head 30, which lowers the volume or space in the bottom of reactor 5 compared to that if simply pressure head 31 was used.

Other schematic details which are shown in FIG. 2 include the catalyst bed, which is disposed in various catalyst tubes as indicated by 32. The salt bath circulation around the tubes is shown by 33. The point where the gases leave the catalyst beds is indicated by the mesh to support the catalyst in the tubes — that is, item 34. The direction of effluent gas flow from the oxidizer reactor tubes is indicated by line 35.

A preferred means for introducing cooling gases such as recycle reactor off gas is the inlet sparger indicated by 36. The cooling gas inlet is shown by 37, and the outlet for the effluent gas and cooling gas is indicated by 38.

EXAMPLE 1

The following calculated example illustrates how maleic anhydride can be produced from butane without appreciable postreaction oxidation to undesirable by-products.

Referring to FIG. 1, fresh make-up air, 43,562 parts per hour (all parts are by weight unless indicated otherwise) is introduced via line 2 and is combined with 5,222 parts per hour of fresh 95% n-butane from line 1 and with 156,172 parts per hour recycle gas from line 3. The combined gas stream, containing 9.1% oxygen and 6.2% butane, at 415° F and 39 psig pressure is fed to the reactor 5 through line 4. The reactor consists of a large vessel containing a multiplicity of tubes, each containing a charge of catalyst pellets. About 25% of the n-butane charge is oxidized to maleic anhydride.

Immediately below the catalyst tubes, but still within the reactor vessel, the off-gases at 705° F pass over heat exchanger 6 and are cooled to 550° in 0.9 second or less. These cooled gases pass out of the reactor via line 7 at 24 psig. Further cooling to 275° F is carried out in heat exchanger 8. The reactor effluent in line 9, 204,856 parts per hour at 275° F and 22 psig, is fed into the absorber 10. Organic absorbent containing 0.1% maleic anhydride is fed to the absorber via line 17.

The maleic anhydride-enriched stream, 40,392 parts per hour containing 2,709 parts of maleic anhydride, passes from absorber 10 to stripper 19 via line 18. In the stripper, the maleic anhydride, except for 0.1% is removed from the organic absorbent and is withdrawn through line 20 to be purified by distillation. Ultimate recovery is 2,659 parts per hour of 99.9% pure maleic anhydride. The maleic anhydride lean absorbent is recycled back to the absorber through line 17.

The reactor effluent gas after passing through the absorber 10 flows through line 11 at a temperature of 160° F and under 21 psig of pressure. This gas stream, 202,089 parts per hour and containing 27 parts of absorbent, is then washed in scrubber 12 with 45,526 parts per hour of water from line 13. The wash water, containing 124 parts of light acids, 59 parts of maleic anhydride and 27 parts of organic absorbent, passes to a water treatment zone via line 14 at 49,680 parts per hour.

The maleic anhydride free and water scrubbed effluent gases at 105° F and 20 psig are removed from the scrubber through line 15 at 197,935 parts per hour. This stream is divided into two parts. One portion, 41,763 parts per hour containing 2,024 parts of butane, is a bleed stream and can be processed to recover n-butane or can be utilized as a fuel-containing stream to a stream generator. The remainder of the gas stream 156,172 parts per hour having an oxygen content of 5.5%, is recycled back to the reactor via line 3.

EXAMPLE 2

Under similar conditions, but with the heat exchanger 6 nonoperative, in accordance with our data, we calculated an overall increase in butane conversion from 25% to about 70%. However, yield of maleic anhydride was not increased, rather the additional butane converted produced acetaldehyde, formaldehyde, acrolein, acrylic acid, formic acid and dark-colored compounds which increase the difficulty in obtaining pure maleic anhydride in the purification zone. Furthermore, solid by-products accumulate in the water scrubber.

EXAMPLE 3

At atmospheric pressure, the conversion of butane and the yield of maleic anhydride are not affected by the use of heat exchanger 6, up to gas temperatures as high as 800° F. The crude maleic anhydride product obtained at atmospheric pressure is essentially the same as obtained at high pressure with cooling of the effluent gas by heat exchanger 6 as described in Example 1.

The above examples illustrate the unexpected benefits to be obtained by rapidly cooling the oxidizer off-gas to a temperature below 675° F, preferably below 625° F.

EXAMPLE 4 (Runs 1–59)

Table I below summarizes data obtained from a laboratory maleic anhydride production reactor downstream of which there was added a quartz-lined empty vessel to provide postreactor volume and hence postreactor residence time, which would simulate post-reactor residence times expected in a full-scale plant.

The maleic anhydride production reactor contained a catalyst comprising vanadium and phosphorus oxides. The feed to this reactor was about 2.5% normal butane in air. In the catalyst-filled reactor about 20% of the butane was converted to maleic anhydride. The effluent gases left the maleic anhydride production reactor catalyst bed at about 700° F.

These effluent gases were conducted to the quartz-lined vessel which provided postreactor empty volume and residence time. The vessel was quartz lined to minimize quenching of the post-catalyst reaction by the vessel surface, as hydrocarbon oxidation reactions are quenched by metal surfaces. Thermal quenching of the post-catalyst oxidation occurs in the laboratory reactor, as there is substantial cooling of the reacting gases by heat transfer to the vessel surface. In the commercial plant, there will be little heat loss through the reactor wall or the transfer lines, so that reaction, once initiated, should be more extensive.

The gases passed to the quartz-lined vessel via an insulated duct and a 2 feet long preheater coil which was about ¼ in. inside diameter. Residence time in the preheater coil and the insulated duct were less than about 1/10 second. The preheater coil was necessary to make up for any heat losses in the postreactor laboratory set-up, as substantial heat losses do not occur in commercial practice for the volume space immediately subsequent to the reactor catalyst bed. Also the preheater coil allowed temperature control for studying, if desired, somewhat higher temperatures than in the catalyst-filled reactor. A cylindrical aluminum block 6.25 in. in diameter by 8 in. high was cast around the preheater coil and the quartz-lined postreactor vessel. Heat to the aluminum block was provided by two 500-watt Watlow band heaters. Thermocouples were placed in the insulated duct, the quartz-lined postreactor vessel, and two in the aluminum block.

The quartz-lined postreactor vessel was 2 in. in diameter by 3 in. long and had a volume of about 166 ml. To analyze for normal butane decomposition in the quartz-lined vessel a controlled bleed stream was taken from ahead of the quartz-lined vessel, and its analysis was compared to the analysis of the stream emerging from the quartz-lined vessel. Analysis was by chromatograph.

Table I lists several of the operating variables and the results in terms of normal butane decomposition. Thus, Table I lists run numbers, residence time (R/T) in the quarts-lined vessel in seconds (to calculate the residence time the normal cubic feet per minute feed rate was corrected to actual temperature and pressure), cast aluminum block temperature in °F, quartz-lined vessel inside chamber temperature in °F (for several runs such as Run No. 28 the chamber temperature is higher than the block temperature because of substantial butane decomposition), the pressure in the quartz-lined vessel, the oxygen concentration from the quartz-lined vessel, the concentration of normal butane by weight percent in the feed to the quartz-lined vessel, the feed rate in normal cubic feet per minute to the quartz-lined vessel, and lastly the amount of normal butane decomposition, if any, in the quartz-lined vessel, which decomposition was determined by analysis of streams taken before and after the vessel as previously indicated.

reactor temperatures below 625° F and still better below 580° F, more completely and consistently avoided decomposition of normal butane in the postreactor space. We have also determined that residence times, $t_o$, of about 6/10 second and below, more generally below about 0.5 to 1 second, are advantageous between the exit point from the catalyst bed and the point at which cooling to below 675°-580° F has been accomplished): in accordance with the present invention the effluent gases from the catalyst bed is cooled below 675° to 580° F within 0.5 to 1 second.

We have found that at atmospheric pressure and at temperatures up to about 890° F, there is substantially no gas phase decomposition of normal butane.

We claim:

1. In a process for the conversion of normal butane to

TABLE I

| Run No. | R/T, Sec. | Block, °F | Chamber, °F | psig | Outlet, $O_2$, % | Feed $C_4$, % | Feed Rate NCFM | Decomposition n$C_4$, % |
|---|---|---|---|---|---|---|---|---|
| 1 | 0.75 | 485 | 483 | 30.6 | 7.4 | 2.24 | 0.81 | 1.5 |
| 2 | 0.75 | 485 | 485 | 30.6 | 7.4 | 2.23 | 0.81 | 0 |
| 3 | 0.74 | 500 | 500 | 30.8 | 7.6 | 2.19 | 0.81 | 0 |
| 4 | 0.71 | 550 | 549 | 31.0 | 7.3 | 2.20 | 0.81 | 0 |
| 5 | 0.70 | 551 | 549 | 31.0 | 7.3 | 2.25 | 0.82 | 0 |
| 6 | 0.70 | 552 | 552 | 31.0 | 7.0 | 2.27 | 0.82 | 0 |
| 7 | 0.70 | 557 | 556 | 31.0 | 7.0 | 2.20 | 0.81 | 0 |
| 8 | 0.67 | 599 | 592 | 30.9 | 7.4 | 2.36 | 0.81 | 0 |
| 9 | 0.67 | 598 | 593 | 30.9 | 7.5 | 2.39 | 0.81 | 0 |
| 10 | 0.66 | 600 | 599 | 30.9 | 7.5 | 2.39 | 0.82 | 0 |
| 11 | 0.66 | 599 | 599 | 30.9 | 7.4 | 2.38 | 0.82 | 0 |
| 12 | 0.66 | 599 | 595 | 30.9 | 7.5 | 2.38 | 0.82 | 0 |
| 13 | 0.65 | 651 | 650 | 30.6 | 7.4 | 2.40 | 0.80 | 2.0 |
| 14 | 0.64 | 651 | 651 | 30.5 | 7.4 | 2.41 | 0.81 | 0 |
| 15 | 0.64 | 651 | 651 | 30.5 | 7.4 | 2.41 | 0.81 | 0 |
| 16 | 0.62 | 671 | 671 | 30.0 | 7.2 | 2.43 | 0.81 | 1.5 |
| 17 | 0.62 | 675 | 673 | 30.0 | 7.4 | 2.46 | 0.81 | 1.4 |
| 18 | 0.62 | 670 | 668 | 30.0 | 7.4 | 2.46 | 0.81 | 0.5 |
| 19 | 0.62 | 670 | 668 | 30.0 | 7.4 | 2.49 | 0.81 | 0 |
| 20 | 0.62 | 677 | 695 | 30.1 | 7.2 | 2.43 | 0.81 | 6.4 |
| 21 | 0.61 | 679 | 699 | 30.0 | 7.2 | 2.50 | 0.81 | 8.8 |
| 22 | 0.61 | 678 | 698 | 30.0 | 7.3 | 2.48 | 0.81 | 8.9 |
| 23 | 0.61 | 678 | 698 | 30.0 | 7.3 | 2.50 | 0.81 | 8.0 |
| 24 | 0.61 | 685 | 715 | 30.0 | 7.4 | 2.51 | 0.81 | 12.8 |
| 25 | 0.61 | 684 | 715 | 30.0 | 7.4 | 2.52 | 0.81 | 13.7 |
| 26 | 0.61 | 685 | 715 | 30.0 | 7.4 | 2.50 | 0.81 | 14.6 |
| 27 | 0.61 | 685 | 715 | 30.0 | 7.4 | 2.52 | 0.81 | 13.1 |
| 28 | 0.59 | 690 | 725 | 30.1 | 7.6 | 2.62 | 0.83 | 15.8 |
| 29 | 0.59 | 698 | 731 | 30.1 | 7.6 | 2.61 | 0.83 | 15.4 |
| 30 | 0.59 | 701 | 738 | 30.1 | 7.7 | 2.55 | 0.83 | 14.6 |
| 31 | 0.59 | 700 | 737 | 30.1 | 7.8 | 2.59 | 0.83 | 14.7 |
| 32 | 0.41 | 680 | 682 | 30.0 | 7.6 | 2.50 | 1.22 | 0 |
| 33 | 0.41 | 680 | 682 | 30.0 | 7.5 | 2.50 | 1.22 | 0 |
| 34 | 0.41 | 678 | 675 | 30.0 | 7.2 | 2.53 | 1.22 | 0 |
| 35 | 0.41 | 678 | 674 | 30.0 | 7.2 | 2.55 | 1.22 | 0 |
| 36 | 0.40 | 689 | 695 | 30.5 | 7.6 | 2.49 | 1.23 | 1.9 |
| 37 | 0.40 | 690 | 697 | 30.5 | 7.6 | 2.47 | 1.23 | 2.4 |
| 38 | 0.40 | 690 | 700 | 30.5 | 7.5 | 2.55 | 1.23 | 2.8 |
| 39 | 0.40 | 690 | 710 | 30.5 | 7.5 | 2.54 | 1.23 | 3.3 |
| 40 | 0.40 | 700 | 725 | 30.0 | 7.3 | 2.46 | 1.23 | 9.2 |
| 41 | 0.40 | 700 | 725 | 30.6 | 7.5 | 2.50 | 1.23 | 8.7 |
| 42 | 0.40 | 700 | 725 | 30.6 | 7.5 | 2.49 | 1.23 | 8.3 |
| 43 | 0.40 | 700 | 725 | 30.5 | 7.5 | 2.45 | 1.24 | 9.1 |
| 44 | 0.40 | 709 | 735 | 30.4 | 7.3 | 2.48 | 1.23 | 8.2 |
| 45 | 0.40 | 709 | 734 | 30.4 | 7.3 | 2.49 | 1.22 | 10.4 |
| 46 | 0.40 | 710 | 734 | 30.4 | 7.4 | 2.48 | 1.22 | 9.5 |
| 47 | 0.40 | 710 | 733 | 30.3 | 7.5 | 2.50 | 1.22 | 8.3 |
| 48 | 0.58 | 680 | 672 | 24.0 | 7.6 | 2.57 | 0.74 | 0 |
| 49 | 0.58 | 680 | 672 | 24.0 | 7.6 | 2.55 | 0.74 | 0 |
| 50 | 0.60 | 680 | 676 | 24.0 | 7.5 | 2.56 | 0.72 | 0 |
| 51 | 0.60 | 680 | 677 | 24.0 | 7.5 | 2.57 | 0.72 | 0 |
| 52 | 0.58 | 700 | 720 | 24.0 | 7.6 | 2.50 | 0.73 | 9.3 |
| 53 | 0.58 | 700 | 720 | 24.0 | 7.6 | 2.53 | 0.73 | 10.2 |
| 54 | 0.58 | 700 | 721 | 24.0 | 7.5 | 2.55 | 0.73 | 8.0 |
| 55 | 0.58 | 700 | 721 | 24.0 | 7.5 | 2.56 | 0.73 | 8.9 |
| 56 | 1.00 | 651 | 644 | 24.0 | 7.4 | 2.50 | 0.44 | 2.0 |
| 57 | 1.00 | 650 | 647 | 24.0 | 7.4 | 2.49 | 0.44 | 5.4 |
| 58 | 1.00 | 650 | 642 | 24.0 | 7.5 | 2.53 | 0.44 | 0 |
| 59 | 1.00 | 650 | 643 | 24.0 | 7.4 | 2.54 | 0.44 | 2.8 |

As can be seen from runs 13 to 19 and 48 to 51 in Table I, we found little decomposition of normal butane in the postreactor space if the temperature was maintained below about 675° F for pressures of about 24 to 30 psig and residence time of about 6/10 second. Post maleic anhydride at a pressure between about 15 and 100 psig and a temperature above 675° F, by contacting the normal butane with oxygen-containing gas an an oxidation catalyst disposed in a fixed catalyst bed or set of tubes in a reactor vessel, and withdrawing an effluent comprising unreacted normal butane, oxygen and maleic anhydride from the catalyst bed or tubes, the improvement which comprises cooling the effluent below 675° F before the effluent is withdrawn from the reactor vessel.

2. A process in accordance with claim 1, wherein maleic anhydride is recovered from the reactor effluent in an organic recovery system.

3. A process in accordance with claim 1 wherein the effluent is cooled below 675° F by heat exchange with a cooling fluid passed through cooling coils in the bottom of the reactor vessel.

4. A process in accordance with claim 1 wherein the effluent is cooled by mixing the effluent with a nonaqueous cooling gas before the effluent is withdrawn from the reactor vessel.

5. A process in accordance with claim 4, wherein the cooling gas is a portion of reactor recycle gas, a portion of the oxygen-containing gas, or a portion of the reactor vessel effluent after said effluent has been cooled at least 50° F.

6. A process in accordance with claim 2, wherein the pressure is above 20 psig.

7. A process in accordance with claim 6, wherein the temperature to which the effluent is cooled is below 625° F and the catalyst bed temperature is 700° to 850° F.

8. A process in accordance with claim 6, wherein the temperature to which the effluent is cooled is below 580° F.

9. In a process for the convention of normal butane to maleic anhydride at a pressure between about 15 and 100 psig and a temperature above 675° F, by contacting the normal butane with oxygen-containing gas and an oxidation catalyst disposed in a fixed catalyst bed or set of tubes in a reactor vessel, and withdrawing an effluent comprising unreacted normal butane, oxygen and maleic anhydride from the catalyst bed or tubes, the improvement which comprises cooling the effluent below 675° F within one second time after withdrawal of the effluent from the catalyst bed said cooling being completed before the effluent is withdrawn from the reactor vessel.

10. In a process for the conversion of normal butane to maleic anhydride at a pressure between about 15 and 100 psig and a temperature above 675° F, by contacting the normal butane with oxygen-containing gas and an oxidation catalyst disposed in a fixed catalyst bed or set of tubes in a reactor vessel, and withdrawing an effluent comprising unreacted normal butane, oxygen and maleic anhydride from the catalyst bed or tubes, the improvement which comprises cooling the effluent below 675° F within a time, $t_1$, after withdrawal of the effluent from the catalyst bed, wherein $t_1$ is given by the following equation:

$$t_1 = 1.4 \times 10^{-6} \exp(14350/T)$$

said cooling being completed before the effluent is withdrawn from the reactor vessel.

11. A process in accordance with claim 10 wherein the reactor pressure is between 15 and 35 psig, the butane in the total feed to the reactor is between 1 and 3 volume %, and the oxygen concentration in the reactor effluent in the range 5 to 10 volume %.

* * * * *